(12) United States Patent
Cairns et al.

(10) Patent No.: US 7,959,290 B2
(45) Date of Patent: Jun. 14, 2011

(54) SCANNING OPHTHALMOSCOPES

(75) Inventors: David John Cairns, Kinross (GB);
Robert Barnet Henderson, Dalgety Bay (GB)

(73) Assignee: Optos PLC, Fife (GB)

( * ) Notice: Subject to any disclaimer, the term of this patent is extended or adjusted under 35 U.S.C. 154(b) by 0 days.

(21) Appl. No.: 12/373,857

(22) PCT Filed: Jun. 13, 2007

(86) PCT No.: PCT/GB2007/002208
§ 371 (c)(1),
(2), (4) Date: Jan. 29, 2010

(87) PCT Pub. No.: WO2008/009877
PCT Pub. Date: Jan. 24, 2008

(65) Prior Publication Data
US 2010/0141895 A1    Jun. 10, 2010

(30) Foreign Application Priority Data
Jul. 15, 2006 (GB) .................................. 0614136.0

(51) Int. Cl.
*A61B 3/14* (2006.01)
*A61B 3/10* (2006.01)
*A61B 3/00* (2006.01)

(52) U.S. Cl. .................. 351/206; 351/221; 351/246

(58) Field of Classification Search ........... 351/200–246
See application file for complete search history.

(56) References Cited

U.S. PATENT DOCUMENTS

| 5,268,711 | A | * | 12/1993 | Poxleitner et al. ............ 351/214 |
| 5,815,242 | A | * | 9/1998 | Anderson et al. ............. 351/221 |
| 5,984,474 | A | | 11/1999 | Schweitzer et al. .......... 351/205 |
| 6,262,849 | B1 | * | 7/2001 | Potin et al. .................... 359/631 |

FOREIGN PATENT DOCUMENTS

| EP | 0 412 667 | 2/1991 |
| WO | 90/00026 | 1/1990 |
| WO | 95/13012 | 5/1995 |

* cited by examiner

*Primary Examiner* — Mohammed Hasan
(74) *Attorney, Agent, or Firm* — Drinker Biddle & Reath LLP

(57) ABSTRACT

A scanning ophthalmoscope (10) and method is provided for scanning the retina of an eye comprising a source of collimated light (12), a first scanning element (14), a second scanning element (16), scan compensation means (18), wherein the source of collimated light, the first and second scanning elements and the scan compensation means combine to provide a two-dimensional collimated light scan from an apparent point source, and the scanning ophthalmoscope further comprises scan transfer means (20), wherein the scan transfer means has two foci and the apparent point source is provided at a first focus of the scan transfer means and an eye (22) is accommodated at a second focus of the scan transfer means.

29 Claims, 1 Drawing Sheet

SCANNING OPHTHALMOSCOPES

BACKGROUND OF THE INVENTION

The present invention relates to a scanning opthalmoscope for scanning human retinas and a method of scanning the retina of an eye.

An ultra-wide field scanning opthalmoscope for scanning human retinas is described in the Applicant's European Patent No. 0730428.

The system comprises:
1. a slow scan element;
2. a fast scan element;
3. an ellipsoidal main mirror; and
4. a scan compensator.

The slow scan element provides a scanning motion of an incident laser beam, in a first direction. The fast scan element provides a scanning motion of the incident laser beam, in a second direction, orthogonal to the first direction.

The fast scan element is positioned at the first focus point of the ellipsoidal main mirror and the subject's pupil is positioned at the second focus point of the ellipsoidal main mirror. Therefore, light emanating from the first focus point of the mirror is reflected through the second focus point of the mirror, and therefore, through the subject's pupil.

As a result of the apparent or virtual point source, the system enables ultra-wide retinal images of the retina to be obtained. The system enables taking 120 degree external scans through 2 mm undilated pupils.

However, in order to allow transmission of the laser beam, it was found necessary to make modifications to the system described above. The modifications provided a lateral spacing between each of the above-referenced components, and applied a "tilt" to the input laser beam.

This modified system was found to work well, transferring light efficiently over the substantial scan angles. However, the consequence of the tilted input beam was that the scan on the retina had a "shear" component which varies as a function of field position. While this shear distortion does not affect the ability to diagnose pathology, it does impact initial perceptions and the ability to measure consistent dimensions within the retinal images.

It is an object of the present invention to provide an improved scanning opthalmoscope which obviates or mitigates one or more of the disadvantages referred to above.

BRIEF SUMMARY OF THE INVENTION

According to a first aspect of the present invention there is provided a scanning opthalmoscope for scanning the retina of an eye comprising:
  a source of collimated light;
  a first scanning element;
  a second scanning element;
  scan compensation means;
  wherein the source of collimated light, the first and second scanning elements and the scan compensation means combine to provide a two-dimensional collimated light scan from an apparent point source; and
  the scanning opthalmoscope further comprises scan transfer means, wherein the scan transfer means has two foci and the apparent point source is provided at a first focus of the scan transfer means and an eye is accommodated at a second focus of the scan transfer means, and wherein the scan transfer means transfers the two-dimensional collimated light scan from the apparent point source into the eye,
  wherein the rotational axis of the second scanning element is substantially parallel to a line joining the two foci of the scan transfer means, and
  wherein, in the provision of the two-dimensional collimated light scan from the apparent point source, the scan compensation means produces a one-dimensional collimated light scan, and the line joining the two foci of the scan transfer means lies substantially on a plane defined by the one-dimensional collimated light scan produced by the scan compensation means.

The rotational axis of the second scanning element may be within approximately 5° of the line joining the two foci of the scan transfer means. The rotational axis of the second scanning element may be within approximately 2° of the line joining the two foci of the scan transfer means. The rotational axis of the second scanning element and the line joining the two foci of the scan transfer means, may have a degree of parallelism which depends on chosen eccentricities of one or more components of the scanning opthalmoscope. The rotational axis of the second scanning element and the line joining the two foci of the scan transfer means, may have a degree of parallelism determined by a user of the scanning opthalmoscope, according to an acceptable level of shear in images of the retina produced by the opthalmoscope.

The line joining the two foci of the scan transfer means may be within approximately 5° of the plane defined by the one-dimensional collimated light scan produced by the scan compensation means. The line joining the two foci of the scan transfer means may be within approximately 2° of the plane defined by the one-dimensional collimated light scan produced by the scan compensation means. The line joining the two foci of the scan transfer means and the plane defined by the one-dimensional collimated light scan produced by the scan compensation means, may have a degree of coincidence which depends on chosen eccentricities of one or more components of the scanning opthalmoscope. The line joining the two foci of the scan transfer means and the plane defined by the one-dimensional collimated light scan produced by the scan compensation means, may have a degree of coincidence determined by a user of the scanning opthalmoscope, according to an acceptable level of shear in images of the retina produced by the opthalmoscope.

The scan compensation means may comprise an elliptical mirror. The scan compensation means may comprise an aspherical mirror. The scan compensation means may comprise an ellipsoidal mirror. The scan compensation means may comprise a pair of parabola mirrors. The scan compensation means may comprise a pair of paraboloidal mirrors.

The scan transfer means may comprise an elliptical mirror. The scan transfer means may comprise an aspherical mirror. The scan transfer means may comprise an ellipsoidal mirror. The scan transfer means may comprise a pair of parabola mirrors. The scan transfer means may comprise a pair of paraboloidal mirrors.

The scan compensation means may comprise two foci. One foci of the scan compensation means may be coincident with one foci of the scan transfer means.

The first scanning element may comprise a rotating mechanism. The first scanning element may comprise a rotating polygon mirror.

The first scanning element may comprise an oscillating mechanism.

The second scanning element may comprise an oscillating mechanism. The second scanning element may comprise an oscillating plane mirror.

The second scanning element may comprise a rotating mechanism. The second scanning element may comprise a rotating plane mirror.

The source of collimated light may comprise a laser light source. The source of collimated light may comprise a light emitting diode.

The scanning opthalmoscope may be able to produce up to 150 degree scans, for example 120 degrees, 110 degrees, 90 degrees, 60 degrees, 40 degrees, of the retina of the eye, measured at the pupillary point of the eye. The scanning opthalmoscope may be able to produce such scans of the retina of the eye, through a 2 mm undilated pupil of the eye.

According to a second aspect of the present invention there is provided a method of scanning the retina of an eye comprising the steps of:
 providing a source of collimated light, a first scanning element, a second scanning element and a scan compensation means;
 using the source of collimated light, the first and second scanning elements and the scan compensation means in combination to provide a two-dimensional collimated light scan from an apparent point source;
 providing a scan transfer means having two foci;
 positioning the second scanning element such that its rotational axis is substantially parallel to a line joining the two foci of the scan transfer means;
 providing the apparent point source at a first focus of the scan transfer means and accommodating the eye at the second focus of the scan transfer means;
 using the scan transfer means to transfer the two-dimensional collimated light scan from the apparent point source to the eye,
 wherein in the provision of the two-dimensional collimated light scan from the apparent point source, the scan compensation means produces a one-dimensional collimated light scan, and the line joining the two foci of the scan transfer means lies substantially on a plane defined by the one-dimensional collimated light scan produced by the scan compensation means.

Embodiments of the present invention will now be described, by way of example only, with reference to the accompanying drawing, in which:

DETAILED DESCRIPTION OF EMBODIMENTS OF OF THE INVENTION

Figure 1:
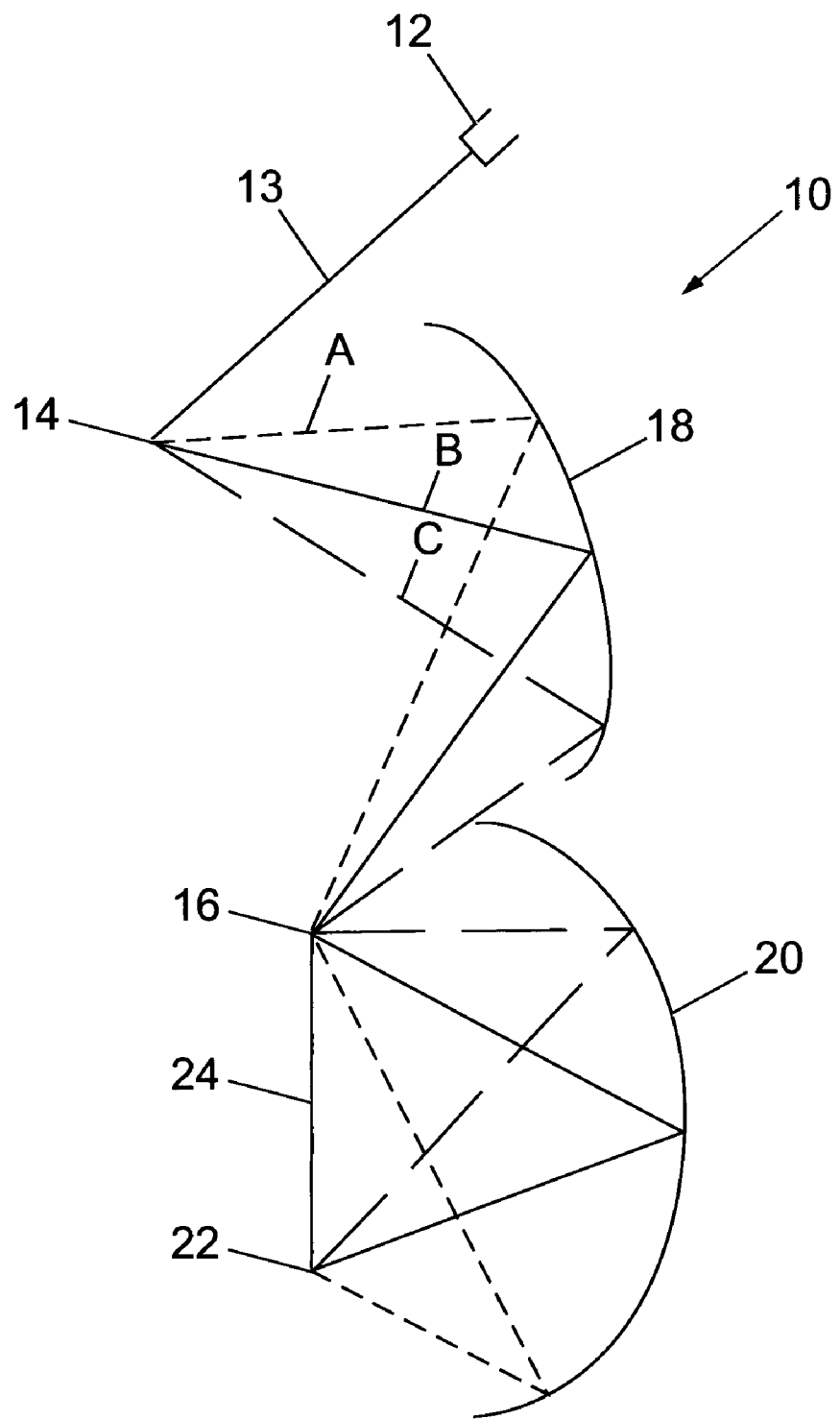
FIG. 1 is an optical schematic of a scan compensation means and scan transfer means of a scanning opthalmoscope according to the present invention, which indicates the incident path from a source of collimated light to a subject's eye.

The scanning opthalmoscope is able to produce 120 degree scans, measured at the pupillary point, through 2 mm undilated pupils. Other scan angles are also possible.

With reference to FIG. 1, the scanning opthalmoscope 10 comprises a source of collimated light which is a laser 12 producing a laser beam 13, a first scanning element 14, a second scanning element 16, scan compensation means 18 and scan transfer means 20.

The first scanning element 14 is a high speed rotating polygon mirror and the second scanning element 16 is a slow speed oscillating plane mirror. The polygon mirror 14 and the oscillating plane mirror 16 are arranged to create a two-dimensional collimated light scan, in the form of a raster scan pattern of the laser beam 13. The polygon mirror 14 has a plurality of facets, and provides a plurality of first one-dimensional collimated light scans, which, in this embodiment of the invention, comprises vertical one-dimensional scans of the laser beam 13. For each polygon mirror rotation, each facet of the polygon mirror 14 generates a vertical scan component of the raster scan pattern.

FIG. 1 illustrates the path of the laser beam 13 in a vertical one-dimensional scan produced by one facet of the polygon mirror 14, as this facet is rotated. Path A is an example of the laser beam reflected from the polygon mirror 14 at the start of the rotation; path B is an example of the laser beam reflected from the polygon mirror 14 at an intermediate point of the rotation; and path C is an example of the laser beam reflected from the polygon mirror 14 at the end of the rotation.

The oscillating plane mirror 16 provides a second one-dimensional collimated light scan, which, in this embodiment of the invention, comprises a horizontal one-dimensional scan of the laser beam 13. This generates a horizontal scan component of the raster scan pattern. The polygon mirror 14 and the oscillating plane mirror 16 thus together create a two-dimensional collimated light scan in the form of the raster scan pattern.

The scan compensation means 18 has two foci. In the embodiment described here the scan compensation means is an ellipsoidal mirror, and is referred to as a slit mirror. It should be appreciated, however, that the scan compensation means 18 may have an alternative form. The polygon mirror 14 is positioned at a first focus of the slit mirror 18 and the oscillating plane mirror 16 is positioned at the second focus of the slit mirror 18.

The scan transfer means 20 is an aspherical mirror in the form of an ellipsoidal mirror, and is referred to as a main mirror. The main mirror 20 has two foci. The oscillating plane mirror 16 is also positioned at a first focus of the main mirror 20. A subject's eye 22 is positioned at a second focus of the main mirror 20.

The laser beam 13 is thus conveyed to the subject's eye 22, via the polygon mirror 14, the slit mirror 18, the oscillating plane mirror 16 and the main mirror 20. The polygon mirror 14, the slit mirror 18, and the oscillating plane mirror 16, combine to provide a two-dimensional collimated light scan, in the form of a raster scan pattern, from an apparent point source. This coupled from the oscillating plane mirror 16 to the subject's eye 22, by the main mirror 20.

A beam reflected from the retina of the subject's eye 22 is conveyed back through the scanning opthalmoscope, and is used to produce an image of the subject's retina.

The scan compensation means 18 serves a number of functions within the scanning opthalmoscope 10.

A first function of the scan compensation means 18 is that of scan transfer of the laser beam 13 from the polygon mirror 14 to the oscillating plane mirror 16. The scan compensation means 18 provides point to point transfer, without introducing any translational component, which would cause failure of the laser beam 13 to enter through the pupil of the subject's eye. Thus the laser beam 13 appears to come from an apparent point source.

Since the polygon mirror 14 is positioned at the first focus of the slit mirror 18, light from the polygon mirror 14 will always be reflected through the second focus of the slit mirror 18, regardless of the angle of deflection of light from the polygon mirror 14 onto the slit mirror 18. The effect of this is that the raster scan pattern of the laser beam 13 is transmitted without disruption through the pupil of the subject's eye 22. This enables ultra-wide retinal images of the retina to be obtained.

A second function of the scan compensation means 18 is that of a scan angle amplifier. An inherent problem with ultra-wide field laser scanning opthalmoscopes is the difficulty in achieving rapid deflection of the laser beam when creating the raster scan pattern over the required angular range. The element normally used to produce the "fast" part of the raster scan pattern is typically a rotating polygon mirror. For example, a 6-sided polygon mirror can clearly generate 120 degree optical scans. However, if the scan is to be sufficiently fast for acceptable image acquisition rates, the polygon mirror needs to rotate at extremely high speeds. This requires impractically high performance from a polygon mirror scanning system.

In order to create scans of the order of 120 degrees, a polygon mirror with 16 facets may be used. Each facet rotation produces 22.5 degrees of "mechanical" scan and 45 degrees of "optical" scan. Such a polygon mirror can be used with a scan compensation means which provides scan angle amplification. This system allows the rotational speed of the polygon mirror to be reduced, whilst still creating a wide angle raster scan pattern at an acceptable rate.

In the embodiment of the present invention, the polygon mirror 14 comprise 16 facets. Each facet produces a one-dimensional scan of the laser beam 13, comprising a "fan" of laser light rays. These rays travel to the slit mirror 18. The rays are then brought to focus at the oscillating plane mirror 16. According to the eccentricity of the slit mirror 18, there will be scan angle amplification. For example, in order to achieve scan angles of the order of 120 degrees, the scan angle amplification provided by the slit mirror 18 should be approximately three times the input angle, i.e. approximately 3×45 degrees.

A third function of the scan compensation means 18 is that it also shapes the laser beam 13, providing static pre-compensation of aberrations introduced by the main mirror 20. This improves the resolution of the retinal images produced by the scanning opthalmoscope 10. Further, when the slit mirror scan compensation means 18 is an ellipsoidal mirror, astigmatisms can be reduced without necessitating a further cylindrical lens.

Judicious matching of eccentricities of the slit mirror 18 and the main mirror 20 provides well behaved deviation from perfect scan linearity. Symmetric deviation, as a function of angle from the optic axis of the eye, enables simple compensation of distance measurements on the retina in software, and an adequately intuitive retinal display representation.

In the present invention, the components of the scanning opthalmoscope 10 are arranged such that the rotational axis of the oscillating plane mirror 16 is substantially parallel to a line 24 joining the two foci of the main mirror 20. Furthermore, in the provision of the two-dimensional collimated light scan from the apparent point source, the polygon mirror 14 produces a one-dimensional scan which is incident on the slit mirror scan compensation means 18. The slit mirror 18 also therefore produces a one-dimensional scan. The components of the scanning opthalmoscope 10 are arranged such that the line 24 joining the two foci of the main mirror 20 lies substantially on a plane defined by the one-dimensional scan produced by the slit mirror 18. This arrangement of components offers a number of advantages.

The key advantage of having the rotational axis of the oscillating plane mirror 16 substantially parallel to the line 24 joining the two foci of the main mirror 20, and the line 24 lying substantially on the plane defined by the one-dimensional scan produced by the slit mirror 18, is that the scanned image of the subject's retina does not have, or has a reduced, "shear" component. This is because the arrangement of the components of the scanning opthalmoscope 10 removes the requirement to provide a "tilt" to the input laser beam 13, thus improving orthogonality between the horizontal and vertical components of the two-dimensional scan and the line 24 joining the two foci of the main mirror 20.

Therefore, it is possible to measure consistent dimensions within retinal images, thus facilitating simpler quantification of feature size within these images.

Another advantage of the arrangement of the components of the scanning opthalmoscope of the present invention, is that it is possible to control the amount of scan angle amplification provided by the slit mirror 18. This may be done by selecting an appropriate portion of the slit mirror 18 to scan the laser beam 13 from the polygon mirror 14 across.

Selecting an appropriate portion of the slit mirror 18 may be done by varying the angle of incidence of the laser beam 13 on the polygon mirror 14, or by rotating the slit mirror 18 relative to the main mirror 20. For example, FIG. 1 illustrates the situation where the two foci of the slit mirror 18 are rotationally offset from the two foci of the main mirror 20, i.e. the polygon mirror 14 is not collinear with the two foci of the main mirror 20. Varying the amount of rotation of the slit mirror 18 affects the portion of the slit mirror 18, and the scan angle amplification which is obtained. Therefore, the scan angle amplification can be controlled. The required number of facets on the polygon mirror 14 may then be selected accordingly. This provides a certain level of flexibility as regards the polygon mirror 14.

It is also possible to vary the scan angle amplification by using a slit mirror with an appropriate eccentricity.

A further advantage of the arrangement of the components of the scanning opthalmoscope 10 of the present invention, is that since all the components of the scanning opthalmoscope can lie in a single plane, manufacturing of the opthalmoscope 10 is simplified, which reduces build time and cost. Furthermore, this arrangement allows greater flexibility in the positioning of the subject's head in relation to the opthalmoscope 10.

Another advantage is that the number of components comprised in the scanning opthalmoscope of the present invention may be reduced, in comparison to previous opthalmoscopes. This increases the optical brightness of the opthalmoscope of the present invention, which is important when obtaining retinal images.

The scanning laser opthalmoscope 10 of the present invention therefore obviates or mitigates the disadvantages of previous proposals.

Modifications and improvements may be made to the above-described scanning opthalmoscope without departing from the scope of the present invention. For example, although the slit mirror scan compensation means 18 has been described above as being an ellipsoidal mirror having two foci, it should be appreciated that the scan compensation means could take other forms. For example, the scan compensation means could comprise an elliptical mirror, a pair of parabolic mirrors, a pair of paraboloidal mirrors or a combination of any of these components. The common technical feature provided by any of these component arrangements is that the scan compensation means comprises two foci and produces a one-dimensional collimated light scan.

Where elliptical components are used in the scan compensation means, it may also be necessary to provide beam compensation elements, such as cylindrical lenses.

Further, although the above described arrangement of the scanning opthalmoscope 10 has the polygon mirror 14 positioned at the first focus of the slit mirror 18 and the oscillating plane mirror 16 located at the second focus of the slit mirror 18, it should be appreciated that the position of the polygon mirror 14 and the oscillating plane mirror 16 may be switched without affecting the operation of the opthalmoscope 10.

Also, although the second scanning element has been described above as an oscillating plane mirror 16, it should be appreciated that this could be a rotating plane mirror.

Furthermore, although the polygon mirror 14 has been described above as providing vertical scanning of the laser beam 13 and the oscillating plane mirror 16 providing horizontal scanning, it should be appreciated that the axes of rotation and oscillation of these two elements could be switched, such that the polygon mirror 14 provides the horizontal scanning of the laser beam 13 and the oscillating plane mirror 16 provides the vertical scanning.

In addition, although the above embodiment of the present invention has been described as providing 120 degree optical scans, it should be appreciated that the opthalmoscope 10 may be configured to provide a lesser or greater angle of optical scan. As described above, this may be achieved, for example, by varying selection of the portion of the slit mirror 18 that the laser beam 13 is scanned across.

Furthermore, although the components of the opthalmoscope 10 have been illustrated in FIG. 1 as lying vertically in line with one another, it should be appreciated that the laser 12, the polygon 14 and the slit mirror 18 may be rotated together about the rotational axis of the oscillating plane mirror 16 without affecting the operation of the opthalmoscope 10. That is, whatever the orientation of the above-referenced components, as long as the line 24 joining the two foci of the main mirror 20 lies substantially on the plane defined by the one-dimensional scan produced by the slit mirror 18, the opthalmoscope 10 will produce an improved retinal image.

Also, although the source of collimated light has been described above as being a laser 12, it should be appreciated that the source of collimated light could be a light emitting diode.

The invention claimed is:

1. A scanning ophthalmoscope for scanning the retina of an eye comprising:
    a source of collimated light;
    a first scanning element;
    a second scanning element;
    a scan compensation device;
    wherein the first scanning element produces a one-dimensional collimated light scan in a first direction;
    wherein the scan compensation device delivers the one-dimensional collimated light scan from the first scanning element onto the second scanning element in such a manner that the scan in the first direction appears to be provided from an apparent point source; and
    wherein the second scanning element produces from the one-dimensional collimated light scan a two-dimensional collimated light scan by scanning in a second direction from the apparent point source;
    wherein the scanning ophthalmoscope further comprises a scan transfer device, wherein the scan transfer device has two foci and the apparent point source is provided at a first focus of the scan transfer device and an eye is accommodated at a second focus of the scan transfer device, and wherein the scan transfer device transfers the two-dimensional collimated light scan from the apparent point source into the eye,
    wherein the rotational axis of the second scanning element is substantially parallel to a line joining the two foci of the scan transfer device, and
    wherein the line joining the two foci of the scan transfer device lies substantially on a plane defined by the one-dimensional collimated light scan produced by the scan compensation device.

2. A scanning ophthalmoscope according to claim 1 in which the rotational axis of the second scanning element is within approximately 5° of the line joining the two foci of the scan transfer device.

3. A scanning ophthalmoscope according to claim 2 in which the rotational axis of the second scanning element is within approximately 2° of the line joining the two foci of the scan transfer device.

4. A scanning ophthalmoscope according to claim 1 in which the rotational axis of the second scanning element and the line joining the two foci of the scan transfer device, has a degree of parallelism which depends on chosen eccentricities of one or more components of the scanning ophthalmoscope.

5. A scanning ophthalmoscope according to claim 1 in which the rotational axis of the second scanning element and the line joining the two foci of the scan transfer device, has a degree of parallelism determined by a user of the scanning ophthalmoscope, according to an acceptable level of shear in images of the retina produced by the ophthalmoscope.

6. A scanning ophthalmoscope according to claim 1 in which the line joining the two foci of the scan transfer device is within approximately 5° of the plane defined by the one-dimensional collimated light scan produced by the scan compensation device.

7. A scanning ophthalmoscope according to claim 6 in which the line joining the two foci of the scan transfer device is within approximately 2° of the plane defined by the one-dimensional collimated light scan produced by the scan compensation device.

8. A scanning ophthalmoscope according to claim 1 in which the line joining the two foci of the scan transfer device and the plane defined by the one-dimensional collimated light scan produced by the scan compensation device, has a degree of coincidence which depends on chosen eccentricities of one or more components of the scanning ophthalmoscope.

9. A scanning ophthalmoscope according to claim 1 in which the line joining the two foci of the scan transfer device and the plane defined by the one-dimensional collimated light scan produced by the scan compensation device, has a degree of coincidence determined by a user of the scanning ophthalmoscope, according to an acceptable level of shear in images of the retina produced by the ophthalmoscope.

10. A scanning ophthalmoscope according to claim 1 in which the scan compensation device comprises an elliptical mirror.

11. A scanning ophthalmoscope according to claim 10 in which the scan compensation device comprises an aspherical mirror.

12. A scanning ophthalmoscope according to claim 11 in which the scan compensation device comprises an ellipsoidal mirror.

13. A scanning ophthalmoscope according to claim 1 in which the scan compensation device comprises a pair of parabola mirrors.

14. A scanning ophthalmoscope according to claim 1 in which the scan compensation device comprises a pair of paraboloidal mirrors.

15. A scanning ophthalmoscope according to claim 1 in which the scan transfer device comprises an elliptical mirror.

16. A scanning ophthalmoscope according to claim 15 in which the scan transfer device comprises an aspherical mirror.

17. A scanning ophthalmoscope according to claim 16 in which the scan transfer device comprises an ellipsoidal mirror.

18. A scanning ophthalmoscope according to claim 1 in which the scan transfer device comprises a pair of parabola mirrors.

19. A scanning ophthalmoscope according to claim 1 in which the scan transfer device comprises a pair of paraboloidal mirrors.

20. A scanning ophthalmoscope according to claim 1 in which the scan compensation device comprises two foci, a first focus coincident with a center from which said one-dimensional scan is produced at said first scanning element, and a second focus coincident with said apparent point source.

21. A scanning ophthalmoscope according to claim 20 in which said second focus of the scan compensation device is coincident with said first focus of the scan transfer device.

22. A scanning ophthalmoscope according to claim 1 in which the first scanning element comprises a rotating mechanism.

23. A scanning ophthalmoscope according to claim 22 in which the first scanning element comprises a rotating polygon mirror.

24. A scanning ophthalmoscope according to claim 1 in which the second scanning element comprises an oscillating mechanism.

25. A scanning ophthalmoscope according to claim 24 in which the second scanning element comprises an oscillating plane mirror.

26. A scanning ophthalmoscope according to claim 1 in which the source of collimated light comprises a laser light source.

27. A scanning ophthalmoscope according to claim 1 which is able to produce up to 150 degree scans of the retina of the eye, measured at the pupillary point of the eye.

28. A scanning ophthalmoscope according to claim 27 which is able to produce 120 degree scans of the retina of the eye, measured at the pupillary point of the eye.

29. A method of scanning the retina of an eye comprising the steps of:
- providing a source of collimated light, a first scanning element, a second scanning element and a scan compensation device;
- using the source of collimated light to produce a one-dimensional collimated light scan in a first direction;
- using the scan compensation device to deliver the one-dimensional collimated light scan from the first scanning element onto the second scanning element in such a manner that the scan in the first direction appears to be provided from an apparent point source;
- using the second scanning element to produce a two-dimensional collimated light scan from the one-dimensional collimated light scan by scanning in a second direction from the apparent point source;
- providing a scan transfer device having two foci; positioning the second scanning element such that its rotational axis is substantially parallel to a line joining the two foci of the scan transfer device;
- providing the apparent point source at a first focus of the scan transfer device and accommodating the eye at the second focus of the scan transfer device;
- using the scan transfer device to transfer the two-dimensional collimated light scan from the apparent point source to the eye;
- wherein the line joining the two foci of the scan transfer device lies substantially on a plane defined by the one-dimensional collimated light scan produced by the scan compensation device.

* * * * *